US00PP32818P2

(12) United States Plant Patent

Robacker et al.

(10) Patent No.: US PP32,818 P2
(45) Date of Patent: Feb. 16, 2021

(54) *ABELIA* PLANT NAMED 99-6-7

(50) Latin Name: ***Abelia* hybrid**
Varietal Denomination: 99-6-7

(71) Applicant: University of Georgia Research Foundation, Inc., Athens, GA (US)

(72) Inventors: Carol Robacker, Peachtree City, GA (US); Sloane Michele Scheiber, Parkesburg, PA (US); Sherrod Baden, Milner, GA (US); Allen Byous, Thomaston, GA (US)

(73) Assignee: University of Georgia Research Foundation, Inc., Athens, GA (US)

( * ) Notice: Subject to any disclaimer, the term of this patent is extended or adjusted under 35 U.S.C. 154(b) by 0 days.

(21) Appl. No.: 16/873,533

(22) Filed: Apr. 30, 2020

(51) Int. Cl.
*A01H 5/02* (2018.01)

(52) U.S. Cl.
USPC ..... Plt./226

(58) Field of Classification Search
USPC ..... Plt./226
See application file for complete search history.

*Primary Examiner* — Annette H Para
(74) *Attorney, Agent, or Firm* — Thomas | Horstemeyer, LLP

(57) ABSTRACT

A new and distinct cultivar of *Abelia* plant named '99-6-7', characterized by a combination of large flower panicles of pink/purple flowers and sepals, earliness to flower, and heavy blooming from May to September.

4 Drawing Sheets

Botanical designation: *Abelia* hybrid.
Cultivar denomination '99-6-7'.

BACKGROUND OF THE INVENTION

The present invention relates to a new and distinct cultivar of the ornamental flowering shrub botanically known as *Abelia* and hereinafter referred to by the varietal denomination '99-6-7'.

The new *Abelia* '99-6-7' is a product of a planned breeding program conducted by the Inventors in Griffin, Ga. The objective of the *Abelia* breeding program is to produce a tough and adaptable drought-tolerant plant with commercial value. This cultivar has significant commercial and home gardener appeal with its attractive foliage, large flower panicles, heavy blooming, pink sepals, and low maintenance requirements. These and other qualities are enumerated herein.

The new *Abelia* '99-6-7' originated from a cross in 1998 between the cultivar *Abelia* 'Edward Goucher' (unpatented female parent) and *Abelia chinensis* (unpatented, male parent). ('Edward Goucher' is a hybrid of *A.* x *grandiflora* and *A. parvifolia* [syn. *A. schumannii*] that was introduced in 1911 by Edward Goucher, USDA.) Seeds from this interspecific cross were sown in 1999. These seedlings were planted in a field plot in Griffin, Ga. (cold hardiness zone 8a) in the fall of 1999, where they were evaluated for flowering and foliage characteristics, plant form and height, cold hardiness and drought tolerance. Plant '99-6-7' was selected and vegetatively propagated by stem cuttings in 2001. In the summer of 2002, '99-6-7', was planted with 14 other selections into a field plot in Griffin, Ga. in a completely randomized design with ten replications per selection. In summer of 2003, '99-6-7' was planted into a field plot in Blairsville, Ga. (cold hardiness zone 7a), along with 10 other selections and the check cultivar *Abelia* 'Rose Creek' (unpatented hybrid from open pollination of *Abelia chinensis* (female parent) with unknown male parent). This plot had six replicates per selection in a randomized complete block design.

Asexual reproduction of the new *Abelia* '99-6-7' using stem cuttings has been continued in Griffin, Ga. since 2001. Clonally propagated plants have been evaluated in Griffin for over 18 years, and in Blairsville over 16 years. In Griffin, height and widths were measured for the first time in March 2004; following measurements, half of the plants were pruned every two years to a height of 40 to 50 cm and half were left unpruned. Height and width data were collected in Griffin every two years prior to pruning. First bloom dates were recorded each year. Winter cold and spring frost damage was assessed each spring in Griffin and Blairsville. Date of first bloom was recorded each year. Observation for disease or insect damage was continuous throughout the summer.

*Abelia* is a genus of 15-30 species and interspecific hybrids that are popular landscape plants. They range from deciduous to evergreen, depending upon the cultivar and the climate. They have attractive, colorful foliage and flower from late spring to autumn. *Abelia* is a low-maintenance shrub that is tolerant of any well-drained soil, has heat and drought tolerance and is resistant to most pests. It thrives in full sun or part shade and can generally be grown in cold hardiness zones 5 through 9. The new *Abelia* '99-6-7' plant is expected to be distributed for landscape use in the U.S. and perhaps in other countries.

SUMMARY OF THE INVENTION

The following traits have been repeatedly observed and represent the characteristics of a new variety, *Abelia* '99-6-7'. The new variety '99-6-7' has not been observed under all possible environmental conditions. The phenotype may vary somewhat with variations in, for example, temperature, light intensity, soil types, and water and fertility levels without, however, any variance in genotype.

Asexual reproduction of the new *Abelia* '99-6-7' by softwood stem cuttings since 2000 has shown that the unique features of this new *Abelia* are stable and reproduced true to type in successive generations.

'99-6-7' plants, along with other *Abelia* cultivars 'Raspberry Profusion', 'Lavender Mist', 'Rose Creek' and 'Edward Goucher' (maternal parent of '99-6-7') have been evaluated since 2002 in field plots at Griffin, Ga. and since 2003 in Blairsville, Ga. 'Raspberry Profusion' and 'Lavender Mist' are full siblings. 'Rose Creek' was used as a standard for comparison as it is a popular cultivar that has *A. chinensis* as a maternal parent. Height and width data were collected in Griffin every year. Half of the plants were pruned every two years, while the other plants were not pruned to provide information on mature size. First bloom dates were recorded each year. Winter cold and spring frost damage was assessed each spring in Griffin and Blairsville. Observation for disease or insect damage was continuous throughout the summer.

Throughout this specification, color names beginning with a small letter signify that the name of that color, as used in common speech, is aptly descriptive. Color names beginning with a capital letter designate values based upon The R.H.S. Colour Chart, 2001 ($5^{th}$ edition) published by The Royal Horticultural Society, London, England.

The following traits have been consistently observed in the original plant of this new variety and in asexually propagated plants grown from stem cuttings in Blairsville, and Griffin, Ga., and, to the best knowledge of the inventors, their combination forms the unique characteristics of the new variety '99-6-7' and set it apart from all other existing varieties of *Abelia* known to the inventors.

1. The most distinctive quality of '99-6-7' is the heavy and continuous display of pink/purple flowers and sepals from May through September.
2. The variety '99-6-7' begins blooming at least a week earlier than most cultivars of *Abelia* (Table 3).
3. The flowers occur in large compound panicles, mostly terminal though some are axillary (FIGS. 1 and 2; Table 4).
4. Sepals and flowers of '99-6-7' are long and narrow (FIGS. 3 and 4; Table 7).

The following traits have been consistently observed in the original plant of this new variety and in asexually propagated plants grown from stem cuttings in Blairsville, and Griffin, Ga., and, to the best knowledge of the inventors, their combination forms the unique characteristics of the new variety '99-6-7' and set it apart from all other existing varieties of *Abelia* known to the inventors.

1. Height and width of '99-6-7' is statistically similar to 'Raspberry Profusion' and 'Lavender Mist', but 'Rose Creek' is shorter (Tables 1-2).
2. The variety '99-6-7' begins blooming earlier than most cultivars of *Abelia*, and, on average, about a week earlier than 'Raspberry Profusion', 'Lavender Mist' and 'Edward Goucher', and five to six weeks earlier than 'Rose Creek' (Table 3).
3. The variety '99-6-7' blooms from May to September, with heavy blooming in May, June, and August in Griffin (FIG. 1).
4. The flowers occur in compound panicles, mostly terminal though some are axillary. The panicles average about 31 cm in length and 11 cm in width. The lengths of 'Lavender Mist' and 'Edward Goucher' are similar to '99-6-7'; 'Raspberry Profusion' is intermediate in length and 'Rose Creek' is the shortest at 6 cm. Panicle width of '99-6-7' is similar to 'Raspberry Profusion' and 'Lavender Mist'; 'Rose Creek' and 'Edward Goucher' are narrower (FIG. 2; Table 4).
5. The number of subpanicles per compound panicle averages about 26 on '99-6-7'. 'Lavender Mist' and 'Edward Goucher' are similar; 'Raspberry Profusion' and 'Rose Creek' have fewer subpanicles (Table 4).
6. Flowers of '99-6-7' and 'Raspberry Profusion' are shades of red-purple or purple; 'Rose Creek' flowers are white. Sepals of '99-6-7', 'Raspberry Profusion' and 'Rose Creek' are red-purple throughout summer; sepals of '99-6-7' turn greyed-orange in the fall while 'Raspberry Profusion' and 'Rose Creek' turn greyed-red (FIGS. 2, 3 and 4; Tables 5 and 6).
7. Flowers of '99-6-7' are narrower than 'Raspberry Profusion' but wider than 'Rose Creek'. Sepals of '99-6-7' are longer and narrower than those on 'Raspberry Profusion' and 'Rose Creek' (Table 7, FIGS. 3 and 4).
8. Field evaluations in Griffin since 2002 have shown very little or no cold damage on '99-6-7'. Plants of '99-6-7' have been evaluated in Blairsville, Ga. in 2004, 2008 and 2011. Minor damage was observed on 2 out of 6 plants in 2004, 3 out of 6 plants in 2008 and 1 out of 4 plants in 2011. 'Edward Goucher' had severe damage on most plants in 2008. Other checks had no damage or minor damage (Table 8).

BRIEF DESCRIPTION OF THE FIGURES

The accompanying colored photographic illustrations show the overall appearance and distinct characteristics of the new cultivar of '99-6-7'. The colors in the photographs are as close as possible with the photographic and printing technology utilized. Colors in the photographs may differ slightly from the color values cited in the detailed botanical description, which accurately describes the colors of the new *Abelia* '99-6-7'.

The photographs labeled

The photographs labeled

The photographs labeled (FIG. 3C). The photographs were taken of plants grown outdoors in the respective locations.

The photographs labeled

DETAILED BOTANICAL DESCRIPTION

The following traits have been consistently observed in the original plant of this new variety and in asexually propagated progeny grown from stem cuttings in Blairsville, and Griffin, Ga., and, to the best knowledge of the inventors, their combination forms the unique characteristics of the new variety '99-6-7'.

Throughout this specification, color names beginning with a small letter signify that the name of that color, as used in common speech, is aptly descriptive. Color names beginning with a capital letter designate values based upon The R.H.S. Colour Chart, 5$^{th}$ edition published by The Royal Horticultural Society, London, England in 2007.

The following observations, measurements, and values describe plants grown in Griffin, Ga. Plant '99-6-7' was propagated from softwood stem cuttings and grown in one-gallon containers prior to planting in field plots. Data are from plants planted and grown in the field since 2002.

Figure 1B:
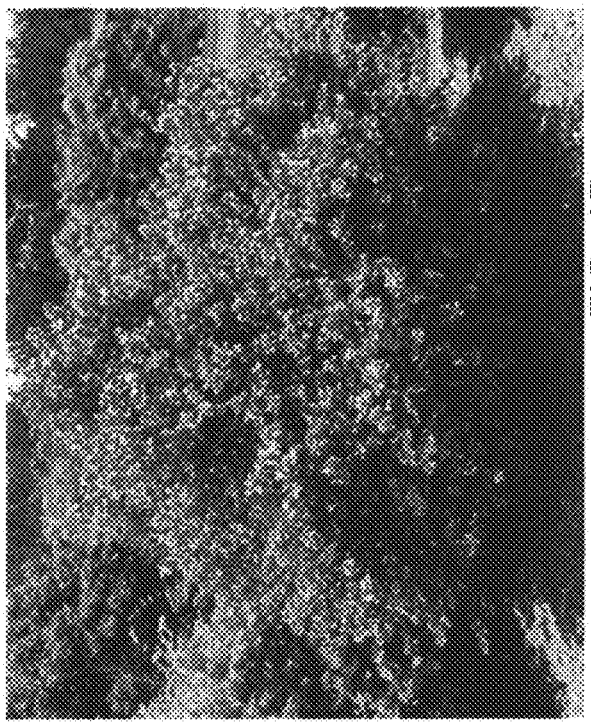
FIGS. 1A-1C depict the overall plant habit of '99-6-7' (FIG. 1A) as compared to 'Raspberry Profusion' (FIG. 1B) and 'Rose Creek' (FIG. 1C). The photographs were taken of plants grown outdoors in Blairsville, Ga. on Jun. 26, 2014.
Figure 1A:
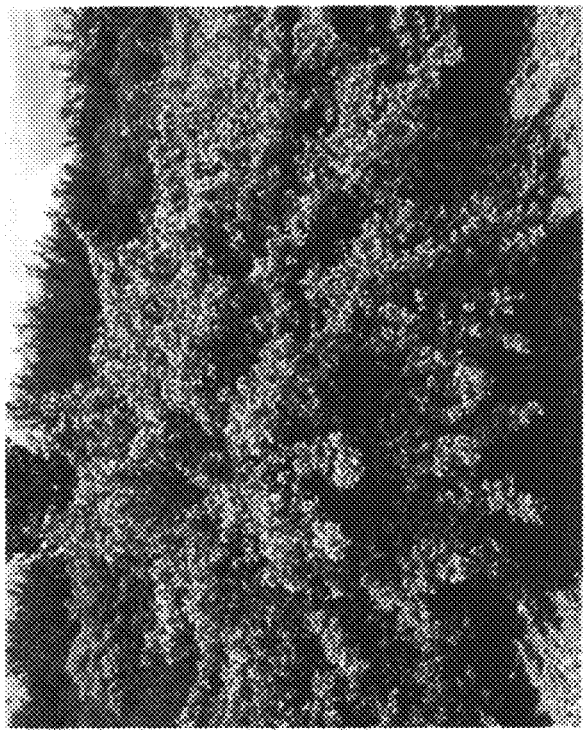
Figure 1C:
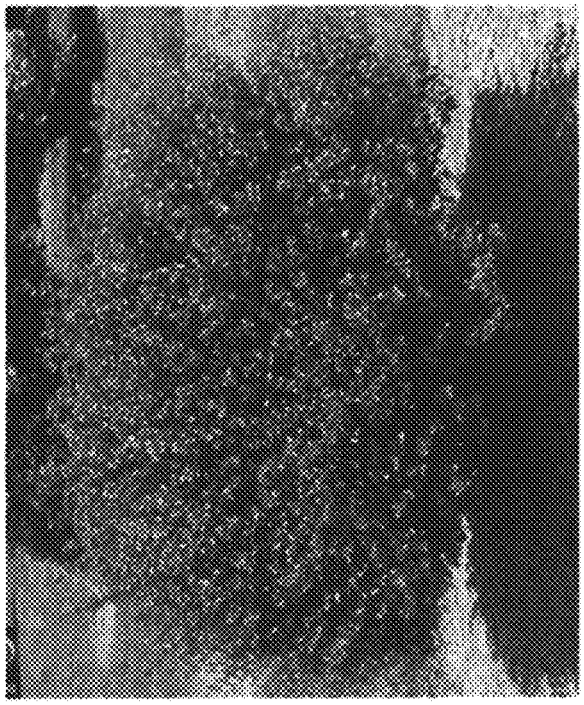

The new variety '99-6-7' has a spreading, upright growth habit. Red-purple flowers and sepals are borne on large compound panicles. Blooming is very heavy from May to September (FIG. 1). The blossoms are highly fragrant. Blooming is heavy even on young plants in containers or in the field.

Figure 2B:
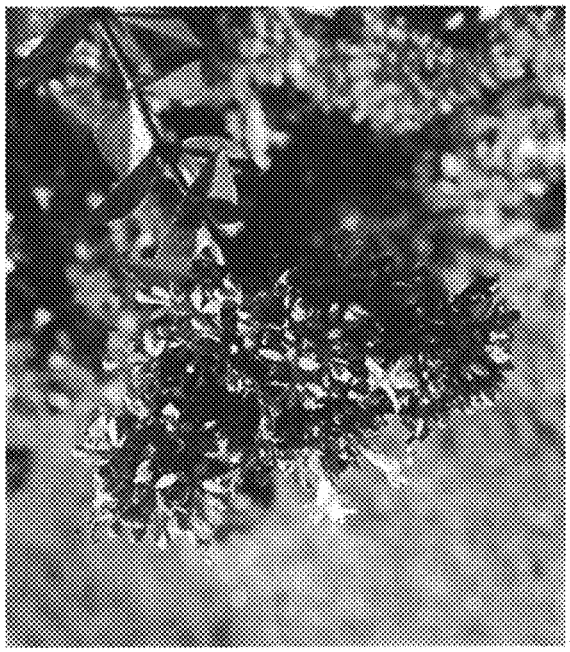
FIGS. 2A-2C depict a close-up view of the compound panicles of '99-6-7' taken on Jul. 25, 2012 (FIG. 2A) as compared to 'Rose Creek' (FIG. 2B) taken on Aug. 8, 2019 and 'Raspberry Profusion' (FIG. 2C) taken on Aug. 8, 2011. The photographs were taken of plants grown outdoors in Griffin, Ga.
Figure 2A:
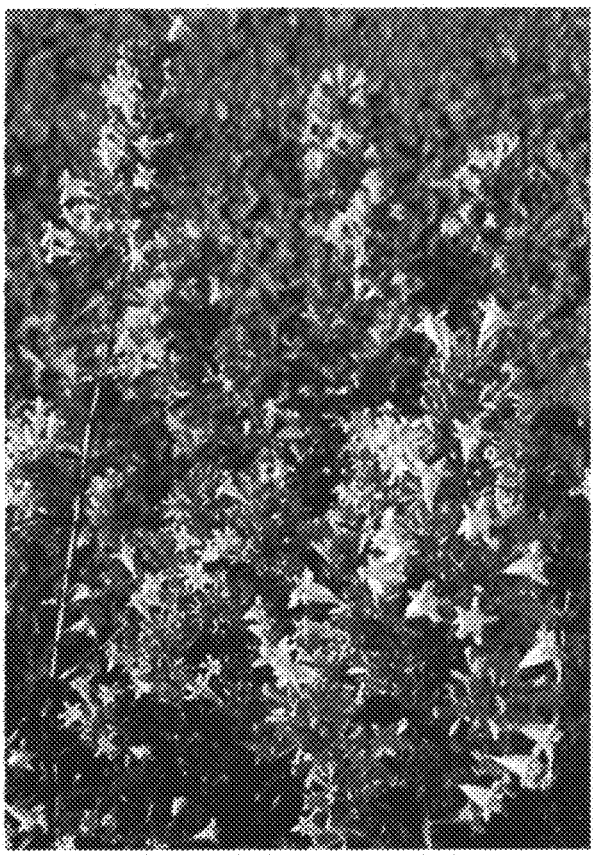
Figure 2C:
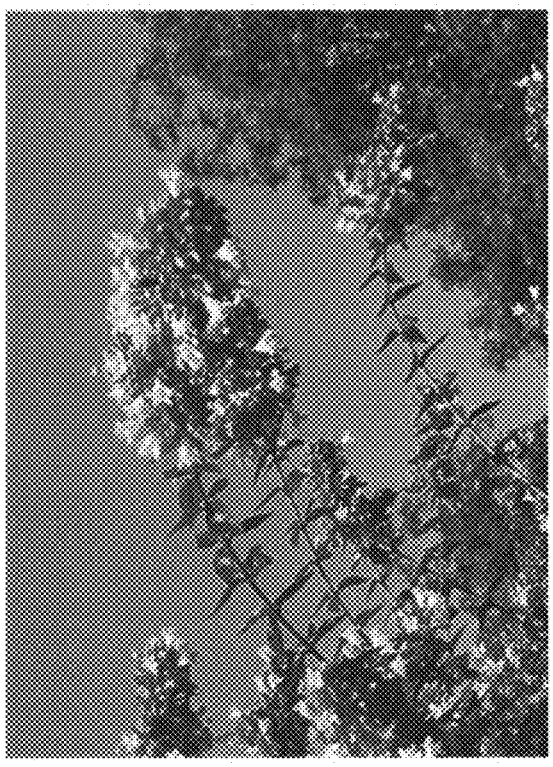
Figure 3B:
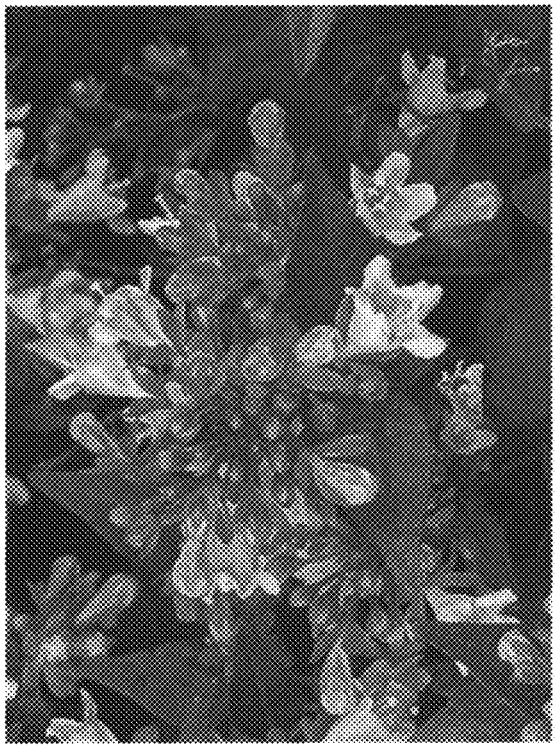
FIGS. 3A-3C depict a close-up view of the flowers and sepals of '99-6-7' on Jun. 14, 2001 in Griffin (FIG. 3A), 'Raspberry Profusion' on May 31, 2012 in Blairsville (FIG. 3B) and 'Rose Creek' on Aug. 8, 2019 in Griffin, Georgia.
Figure 3A:
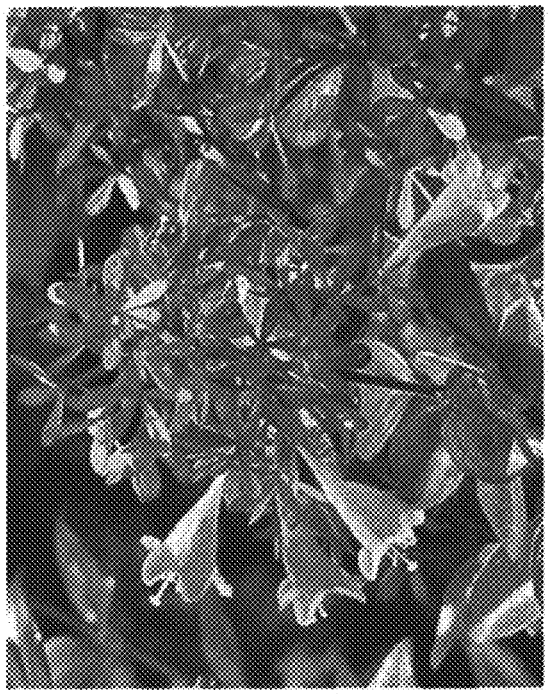
Figure 3C:
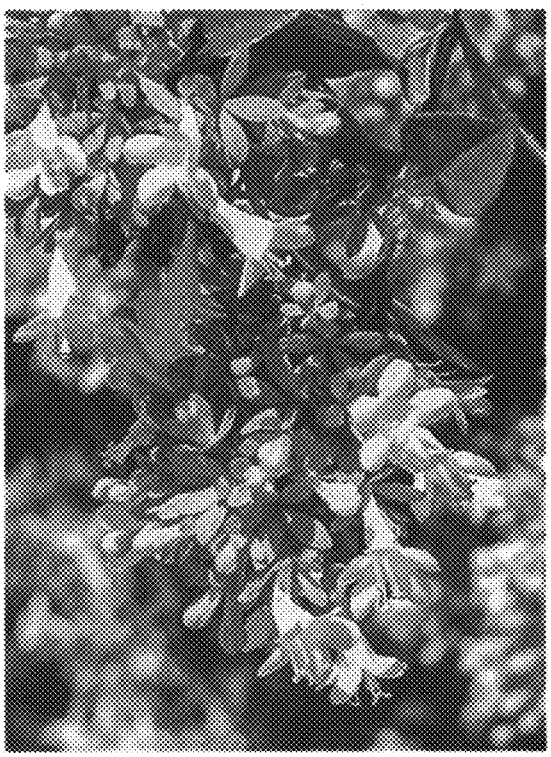
Figure 4B:
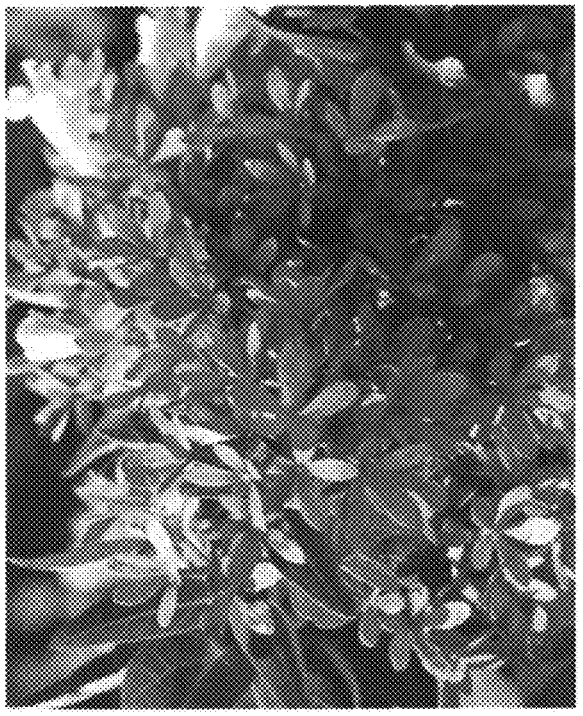
FIGS. 4A-4C depicts a close-up view of the sepals of '99-6-7' (FIG. 4A) and 'Raspberry Profusion' (FIG. 4B), both taken on Sep. 11, 2015 in Griffin, Ga. 'Rose Creek' (FIG. 4C) was taken on Sep. 20, 2005 in Blairsville, Ga. The photographs were taken of plants grown outdoors in the respective locations.
Figure 4A:
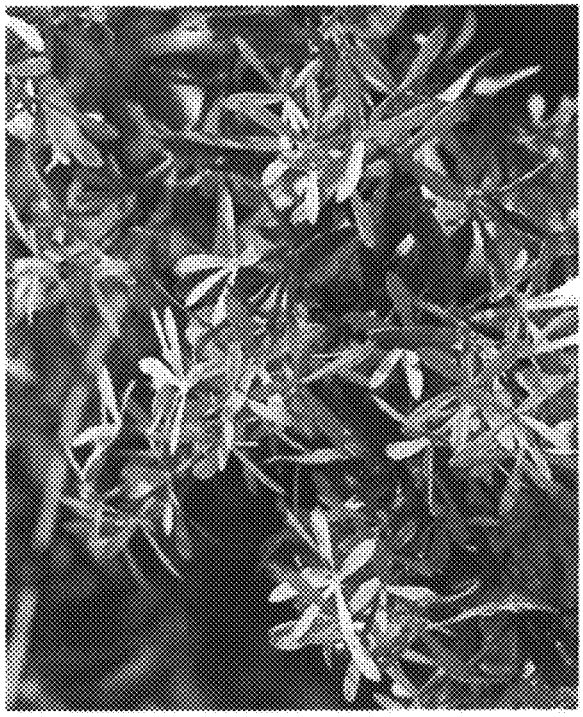
Figure 4C:
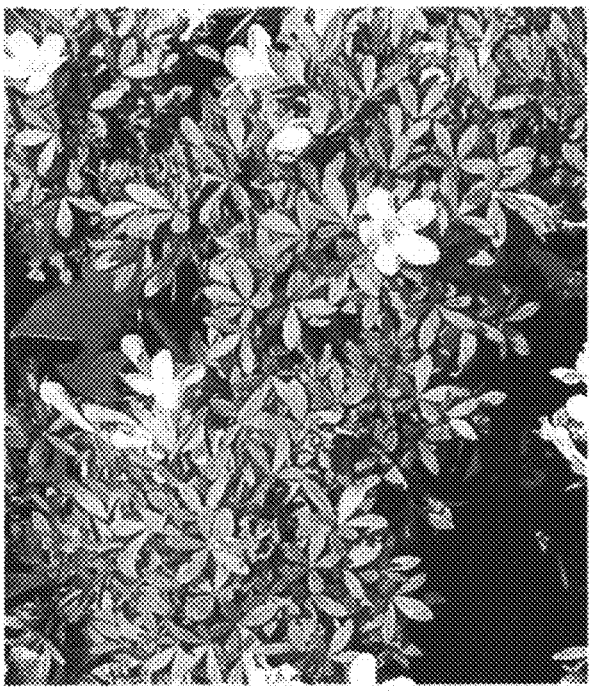

Four checks were used for comparison to '99-6-7': 'Raspberry Profusion', 'Lavender Mist', 'Rose Creek' and 'Edward Goucher'. The panicles of '99-6-7' are significantly longer than those of 'Raspberry Profusion' and 'Rose Creek', and the number of subpanicles per panicle is greater than 'Raspberry Profusion' and 'Rose Creek' (Table 4, FIG. 2). Both upper and lower surfaces of the flower petals are purple on '99-6-7', while 'Rose Creek' has white flowers (Table 5, FIGS. 2 and 3). Sepal color of '99-6-7' is red-purple in the summer, but turns to greyed-orange in the fall. In contrast, the red-purple sepals of both 'Raspberry Profusion' and 'Rose Creek' turn greyed-red in the fall (Table 6, FIG. 4). The new variety '99-6-7' blooms a week earlier than all of the check cultivars, except 'Rose Creek', which blooms a month later (Table 3).

After 16 years growth in a field plot in Griffin, '99-6-7' plants that had not been pruned were an average of 2.8 m tall and 3.6 m wide. Plants that were pruned every two years were 1.5 m tall and 2.3 m wide (Tables 1 and 2). Statistically, 'Rose Creek' was shorter than both pruned and unpruned plants of '99-6-7', and width was also less on pruned plants. The other cultivars were mostly similar in height and width to '99-6-7'.

'99-6-7' is readily propagated through cuttings. Six-inch cuttings taken in May or early June before flowering rooted at a rate of over 70%. After 2 months, cuttings can be transferred to one-gallon containers using a well-drained potting mix. From cutting to saleable plant is about 8 months. No insect or disease problems have been noted in potted plants maintained outside the greenhouse, or in field plants. Once established, the plants are quite drought resistant. After landscape establishment, a hard pruning is recommended in early spring approximately every other year to encourage compact growth and heavy blooming.

The following observations, measurements, and values describe plants of the new *Abelia* '99-6-7' grown in Griffin, Ga. propagated from softwood stem cuttings and grown in one-gallon containers prior to planting in field plots. Data are from plants planted and grown in the field since 2002. Data from Table 8 is taken from plants grown in Blairsville, Ga.

Botanical classification: *Abelia* '99-6-7'.

Commercial classification: Shrub.

Parentage: Initial cross between the cultivar *Abelia* 'Edward Goucher' (unpatented female parent) and *Abelia chinensis* (male parent). ('Edward Goucher' is a hybrid of *A.* x *grandiflora* and *A. parvifolia* [syn. *A. schumannii*] that was introduced in 1911 by Edward Goucher, USDA.)

Growth and propagation:

*Propagation type.*—By softwood stem cuttings and tissue culture.

*Growth rate.*—Softwood cuttings rooted in 3 weeks at an approximate temperature of 80° F. under the mist.

*Root description.*—White, dense, freely branched.

*Rooting habit.*—Fibrous.

Plant description:

*Form.*—Mostly deciduous shrub, upright, peduncles pendulous, foliated, with heavy blooming of pink/purple flowers and sepals.

*Usage.*—Various uses, such as container patio plants, potted plants, landscape uses such as border, hedge, and mass planting.

*Vigor.*—Moderately vigorous.

*Habit.*—Mostly upright, some mature branches arching.

*Size of plant.*—A. Height: about 2.8 m on unpruned plants in field for 16 years. B. Width: about 3.6 m on unpruned plants in field for 16 years.

*Stem.*—Mostly upright, some mature branches arching. A. First Year. 1. Color (RHS) Greyed-Orange N170A. 2. Diameter: Diameter: about 1.6-1.9 mm. 3. Pubescence: Puberulent mix of short and longer hairs, mostly curved. 4. Exfoliation/Texture None. 5. Shape: Round. 6. Pith: a. Type: hollow. b. Diameter: (measured one-half way from apex to start of one year's growth) — about 1.4 mm. c. Color (RHS): Yellow-Green 145D. 7. Odor (of bruised stem): Cut grass (faint). 8. Lenticels. a. Number none observed. 9. Internode length (average of 5 to 10 internodes in middle of first year shoots): about 12 mm. 10. Strength: Very strong. B. Second Year. 1. Color (RHS): Greyed-Orange N170A with Greyed-White 156A striations. 2. Diameter: about 2.5-5 mm. 3. Exfolation/Texture: developing lengthwise cracks along stem.

*Vegetative buds.*—A. Arrangement Opposite or ternary. B. Type Valvate. C. Size (length×width) Approx. 1.5 mm×2 mm. D. Scale Number: 2. E. Scale Color (RHS): Greyed-Purple 184A. F. Position/Disposition (angle to stem) 45°. G. Number at Node 2 vegetative single. H. Pubescence Scattered. I. Shape Lanceolate.

*Leaf scar.*—A. Shape Crescent. B. Vascular Bundle Traces (number, orientation) horizontal across scar. C. Pubescence Short hairs around scar margin. D. Position of Bud (on leaf scar) Directly above central vascular bundle of leaf scar. E. Color Differentiation (RHS) Green 143C. F. Size (h×w) About 1 mm×2 mm.

*Trunk or large stems.*—A. Color(s) (RHS) Greyed-Orange 166B with Greyed-White 156A striation. B. What Size Stem Exfoliation/Begins On about 3-4 mm. C. Diameter about 5-12 mm. D. Texture Somewhat rough, striated, bits of exfoliation present.

*Leaf.*—A. Type Entire. B. Color Through Seasons (always RHS). 1. Emerging: May. a. Upper: Tip is Greyed-Orange 176A; Base is Yellow-Green 146B. b. Lower: Tip is Yellow-Green 147C; Base is Yellow-Green 144A. 2. Summer: August. a. Upper: Green 137B. b. Lower: Yellow-Green 144A. 3. Fall: September. a. Upper Green 137A. b. Lower Green 138B. 4. Winter (dates): December — mostly deciduous, though has newly emergent small leaves. a. Upper Yellow-Green 147A with Brown 200A. b. Lower Yellow-Green 147B. C. Mature Size (L×W): about 3 cm×2.5 cm. D. Apex: Rounded acute. E. Base: Rounded, equilateral. F. Margin: Crenate. G. Shape: Lanceolate. H. Lobes (present/absent): Absent. I. Vein Color (RHS): Yellow-Green 147D. J. Pubescence: 1. Upper Surface: Sparse short hairs along margin. 2. Lower Surface: scattered short hairs along midvein, more concentrated along lower one-third of midvein. K. Arrangement on Stem: Mostly opposite, some trifoliate. L. Venation: Simple alternate. M. Texture. 1. Thickness: 0.3 mm. 2. Degree of waxiness of surfaces: Slightly waxy. N. Odor when Crushed: Faint grassy.

*Petiole*.—A. Length: About 3 mm. B. Shape: Slightly curved and concave. C. Color (RHS): Green 137C. D. Pubescence: Very sparse short curved hairs, mostly on reverse side. E. Diameter: about 1 mm.

*Inflorescence(s)*.—A. Type: Compound panicle, mostly terminal, some axillary. B. Number per Plant: about 500 to 1000, depending upon size of mature plant. C. Size (L×W): about 18-31 cm long, 6-10 cm wide: subpanicles about 7-9 cm long, about 5-6 cm wide. D. Color (RHS): Flowers form continuously throughout the summer. 1. At emergence: Purple 75A. 2. Full bloom: Purple 75A. 3. Fading: Red-Purple 62C. E. Longevity: May to frost. F. Peduncle. 1. Length: Mean 53 cm. 2. Diameter: Mean 5 mm. 3. Color (RHS): Red-Purple 58A. 4. Pubescence: Covered in very short hairs, bracteoles present. 5. Strength: Strong. 6. Aspect: 45° to arching.

*Flower*.—A. Number per Inflorescence: about 250-750 in various stages of bloom. B. Axillary or Terminal: Axillary. C. Symmetry: Regular, actinomorphic. D. Size (L×W): about 14 mm×7 mm. E. Pubescence: Short curved hairs, slightly glandular. F. Texture: Punticulate under scope, many scattered hairs. G. Color at peak of bloom (RHS): 1. Upper Surface: Purple 75A. 2. Lower Surface: Purple 75B. H. Fragrance: Highly floral. I. Time of Full Maturity: Spring. J. Time Range for Showiness Early May until frost. K. Bud. 1. Size (L×W): about 10 mm×3 mm. 2. Shape: Elongated teardrop. 3. Color (RHS): Purple 75A. 4. Pubescence: Covered in very short glandular hairs. 5. Longevity: One week. L. Petals. 1. Number: One. 2. Size (L×W): about 14 mm×7 mm. 3. Shape: Funnel, slightly tubular, gamopetalous. 4. Apex: 5 lobes, rounded and slight curled. 5. Base: Funnel shaped with short tube. 6. Margin: Entire but slightly curled. 7. Color at Peak of Bloom (RHS): a. Upper Surface: Purple 75A. b. Lower Surface: Purple 75B. 8. Texture: Punticulate under scope, many scattered hairs. 9. Arrangement: NA. M. Pedicels. 1. Color (RHS): Red-Purple 58A. 2. Pubescence: Covered in very short hairs. 3. Length: about 1-2 mm. 4. Aspect: 45°. 5. Strength: Medium. N. Sepal(s). 1. Number: Five. 2. Size (L×W): about 7 mm×1.4 mm. 3. Shape: Elliptic. 4. Apex: Rounded. 5. Base: Equilateral. 6. Margin: Entire. 7. Texture: Smooth. 8. Pubescence: Lightly scattered with hairs. 9. Color at peak of bloom (RHS). a. Upper surface: Red-Purple 58D. b. Lower surfaces: Red-Purple 58D. O. Male Reproductive Structures. 1. Number: 4. 2. Anther: Dorsifixed, Revolute. a. Size (L×W): about 1 mm×0.5 mm. b. Shape: Oblong. c. Color (RHS): Yellow-White 158D. d. Texture/Pubescence: Pubescent. 3. Filament. a. Size (L×W): about 10 mm×0.4 mm. b. Color (RHS): White N155B. c. Texture: Smooth with scattered hairs. toward base. 4. Pollen: a. Quantity: Moderate. b. Pollen color (RHS): White N155B. P. Female Reproductive Structures. 1. Pistil. a. Shape: monostylus, free. b. Size (L×W): about 18 mm×1 mm. c. Position (superior, inferior, etc.): Epigynous, ovary inferior. d. Color (RHS): See stigma, style, and ovary below. e. Pubescence: Mostly glabrous, ovary has short curved hairs. 2. Stigma. a. Shape: Circular, slightly domed. b. Color: Orange-White 159 D. c. Pubescence: Glabrous, punticulate. 3. Style a. Length: about 13 mm. b. Shape: tubular. c. Color (RHS): White N155B. d. Pubescence: Mostly glabrous. 4. Ovary. a. Shape: Oval. b. Number: 1. c. Pubescence: Covered in short, curved hairs.

*Fruit*.—A. Type: Achene. B. Size (L×W): about 6 mm×1.5 mm. C. Color(s) During Ripening (RHS): Seeds ripen throughout the summer. 1. Early: Yellow-Green 145A. 2. Mid: Yellow-Green 145A and Red-Purple 63B. 3. Late: Greyed-Orange 174A. D. Shape: Grooved cylindrical capsule. E. Number per Infructescence: 1. F. Pubescence: covered in short hairs. G. Number of Carpels: 1. H. Persistence (effective period): Late spring to frost.

*Inflorescence(s)*.—A. Shape: Cylindrical, grooved longitudinally. B. Size: about 6 mm×1.5 mm. C. Color (RHS): Brown 200D. D. Number per Locule per Ovary per 1. Fruit: E. Germination Capacity: About 30%. F. Pubescence: Covered in short hairs.

TABLE 1

Height and width (cm) of '99-6-7', 'Raspberry Profusion', 'Lavender Mist, 'Rose Creek' and 'Edward Goucher' in a field plot in Griffin, GA in 2018.

| Genotype | Rep # | Height (cm) | Width (cm) |
|---|---|---|---|
| '99-6-7' | 5 | 149.4 ± 11.6* | 231.8 ± 9.3 |
| 'Raspberry Profusion' | 5 | 143 ± 9.7 | 203.6 ± 52.6 |
| 'Lavender Mist' | 4 | 125 ± 18.8 | 221.0 ± 17.3 |
| 'Rose Creek' | 5 | 95.8 ± 6.2 | 164.5 ± 16.7 |
| 'Edward Goucher' | 5 | 133.4 ± 16.7 | 220.8 ± 14.5 |

*Standard error of the means at the 95% confidence level.

Plants were pruned every two years to a height of about 45 to 60 cm, depending upon the maturity of the plant. Data are from plants that were in the field at least 9 years. Reps of '99-6-7', 'Raspberry Profusion', and 'Lavender Mist' were planted in the field in 2002. 'Rose Creek' was planted in 2004, 2006, or 2009. 'Edward Goucher' was planted in 2004, 2005, or 2009.

TABLE 2

Height and width (cm) of '99-6-7', 'Raspberry, 'Lavender Mist, 'Rose Creek' and 'Edward Goucher' in a field plot in Griffin, GA in 2018.

| Genotype | Rep # | Height (cm) | Width (cm) |
|---|---|---|---|
| '99-6-7' | 5 | 283.6 ± 6.5* | 364.3 ± 21.5 |
| 'Raspberry Profusion' | 4 | 267.2 ± 14.1 | 374.9 ± 32.8 |
| 'Lavender Mist' | 6 | 273 ± 4.4 | 437.3 ± 31.0 |

TABLE 2-continued

Height and width (cm) of '99-6-7', 'Raspberry, 'Lavender Mist, 'Rose Creek' and 'Edward Goucher' in a field plot in Griffin, GA in 2018.

| Genotype | Rep # | Height (cm) | Width (cm) |
|---|---|---|---|
| 'Rose Creek' | 4 | 176.2 ± 9.6 | 302.9 ± 51.7 |
| 'Edward Goucher' | 6 | 239.7 ± 23.6 | 380 ± 32.9 |

*Standard error of the means at the 95% confidence level.

Data are from plants that were in the field at least 9 years. Reps of '99-6-7', '99-6-9', and '99-6-11' were planted in 2002. 'Rose Creek' was planted in 2004, 2006 or 2009. 'Edward Goucher' was planted in 2004, 2005 or 2009. These plants were not pruned since field planting.

TABLE 3

Week of first bloom for abelia plants in a Griffin field plot in 2011, 2015 and 2017.

| Genotype | 2011 | 2015 | 2017 |
|---|---|---|---|
| '99-6-7' | 4-25 (10) | 4-27 (5); 5-4 (4); 5-11 (1) | 4-24 (10) |
| 'Raspberry Profusion' | 4-25 (1); 5-2 (8) | 5-4 (3); 5-11 (6) | 5-1 (3); 5-8 (6) |
| 'Lavender Mist' | 4-25 (1); 5-2 (9) | 5-11 (6); 5-18 (4) | 5-1 (4); 5-8 (3); 5-15 (3) |
| 'Rose Creek' | 5-30 (1); 6-6 (9); 6-13 (2) | 6-8 (1); 6-15 (3); 6-22 (2); 6-29 (1) | 5-22 (2); 5-29 (7); 6-5 (2) |
| 'Edward Goucher' | 4-18 (4); 4-25 (6); 5-2 (1) | 5-4 (3); 5-11 (6) | 4-24 (1); 5-1 (5); 5-8 (3) |
| *A chinensis* | 6-6 (1) | 6-15 (1) | 6-5 (1) |

The number in parentheses is the number of plants that bloomed on that date.

TABLE 4

Comparison of morphological traits of '99-6-7', 'Raspberry Profusion', 'Lavender Mist', 'Rose Creek' and 'Edward Goucher'.

| Cultivar | Compound panicle length[1] (mm) | Compound panicle width[1] (mm) | Number of subpanicles per compound panicle |
|---|---|---|---|
| '99-6-7' | 312.4 a[2] | 106.9 abc | 25.6 a |
| 'Raspberry Profusion' | 187.5 b | 109.1 b | 19.3 b |
| 'Lavender Mist' | 327.7 a | 118.8 ab | 21.0 ab |
| 'Rose Creek' | 60.7 c | 94.4 c | 6.3 c |
| 'Edward Goucher' | 295.5 a | 89.2 c | 23.1 ab |

[1]Length and width of compound panicles and number of subpanicles was determined by selecting the ten longest compound panicles on a plant of similar age.
[2]Means of lengths and widths were compared across genotypes using t-tests. Means followed by different letters are significantly different $P < 0.05$.
Data were collected from unpruned field-grown plants in full sun in Griffin, Georgia on Sep. 19, 2019.

TABLE 5

Flower color of '99-6-7', 'Raspberry Profusion'and 'Rose Creek'.

| Cultivar | Petal - upper surface | Petal - lower surface |
|---|---|---|
| '99-6-7' | Purple 75A | Purple 75B |
| 'Raspberry Profusion' | Purple 75A | Red-Purple N74D |
| 'Rose Creek' | White N155C | White N155C |

TABLE 6

Sepal color of '99-6-7', 'Raspberry Profusion' and 'Rose Creek' throughout the flowering season.

| Cultivar | Early summer | Late summer | Fall |
|---|---|---|---|
| '99-6-7' | Red-Purple 58D | Red-Purple 60A | Greyed-Orange 176C |
| 'Raspberry Profusion' | Red-Purple 59D | Red-Purple 60A | Greyed-Red 178B |
| 'Rose Creek' | Red-Purple 59D | Red-Purple 60A | Greyed-Red 178B |

TABLE 7

Sepal length and width (mm) and flower length and width (mm) of 99-6-7, 'Raspberry Profusion' and 'Rose Creek'.

| Cultivar | Sepal length | Sepal width | Flower length | Flower width |
|---|---|---|---|---|
| '99-6-7' | 6.8 a* | 1.4 c | 14.0 a | 7.1 b |
| "Raspberry Profusion' | 5.9 b | 2.8 a | 11.2 b | 9.4 a |
| 'Rose Creek' | 5.6 b | 2.1 b | 11.9 b | 6.4 c |

*Means of lengths and widths were compared across genotypes using t-tests. Means followed by different letters are significantly different $P < 0.01$.
Data is based on a random sample of 20 sepals and flowers from each cultivar.

TABLE 8

Number of plants of '99-6-7' and check cultivars with cold damage in the Blairsville field plot in 2004, 2008, and 2011.

| | No damage | | | Minor damage | | | Severe damage/Dead | | |
|---|---|---|---|---|---|---|---|---|---|
| Genotype | 2004 | 2008 | 2011 | 2004 | 2008 | 2011 | 2004 | 2008 | 2011 |
| '99-6-7' | 4 | 3 | 3 | 2 | 3 | 1 | 0 | 0 | 0 |
| 'Raspberry Profusion' | 6 | 5 | 6 | 0 | 1 | 0 | 0 | 0 | 0 |
| 'Lavender Mist' | 6 | 5 | 5 | 0 | 1 | 1 | 0 | 0 | 0 |
| 'Rose Creek' | 4 | 5 | 5 | 1 | 0 | 0 | 0 | 0 | 0 |
| 'Edward Goucher' | NA | 0 | 0 | NA | 1 | 0 | NA | 3 | 1 |

Plants were classified as having no damage, or minor, moderate or severe damage. None of the cultivars shown here had moderate damage.

What is claimed is:

1. A new distinct cultivar of the *Abelia* plant named '99-6-7' as illustrated as described herein.

* * * * *